（12) United States Patent
Kim et al.

(10) Patent No.: US 11,505,650 B2
(45) Date of Patent: Nov. 22, 2022

(54) POLYMERS AND LUBRICATING COMPOSITIONS CONTAINING POLYMERS

(71) Applicant: Infineum International Limited, Abingdon (GB)

(72) Inventors: Jungyeon Kim, Coventry (GB); Valentin P. Beyer, Kortrijk (BE); Remzi Becer, Coventry (GB); Beatrice N. Cattoz, Bristol (GB); Anthony J. Strong, Oxford (GB); Andrew D. Schwarz, Abington (GB); Daniel J. Phillips, Southam (GB)

(73) Assignee: INFINEUM INTERNATIONAL LIMITED, Abingdon (GB)

( * ) Notice: Subject to any disclaimer, the term of this patent is extended or adjusted under 35 U.S.C. 154(b) by 0 days.

(21) Appl. No.: 17/149,016

(22) Filed: Jan. 14, 2021

(65) Prior Publication Data
US 2021/0214498 A1 Jul. 15, 2021

(30) Foreign Application Priority Data

Jan. 15, 2020 (EP) .................................. 20152066

(51) Int. Cl.
*C08G 73/02* (2006.01)
*C07D 263/14* (2006.01)
*C10M 149/12* (2006.01)

(52) U.S. Cl.
CPC ....... *C08G 73/0233* (2013.01); *C07D 263/14* (2013.01); *C10M 149/12* (2013.01); *C10M 2207/281* (2013.01); *C10M 2209/1003* (2013.01)

(58) Field of Classification Search
CPC .......... C10M 149/12; C10M 2217/044; C10M 2217/04; C10M 2207/281; C10M 2209/1003; C10N 2030/54; C10N 2020/04; C10N 2030/06; C07D 263/14; C08G 73/0233
See application file for complete search history.

(56) References Cited

U.S. PATENT DOCUMENTS 5,439,978 A * 8/1995 Parkinson ............... C08G 73/06 525/185
2017/0355925 A1* 12/2017 Schwarz .............. C10M 149/18
2019/0066891 A1* 2/2019 Zong .................. C08G 73/0233

FOREIGN PATENT DOCUMENTS

EP 3492567 A1 6/2019
EP 3502217 A1 6/2019

OTHER PUBLICATIONS

Valentin P. Beyer et al., Brush Copolymers from 2-Oxazoline and Acrylic Monomers via an Inimer Approach, Macromolecules, vol. 53, No. 8, Apr. 15, 2020, pp. 2950-2958, XP055710795.
Liu et al, Low friction and high load bearing capacity layers formed by cationic-block-non-ionic bottle-brush copolymers in aqueous media, The Royal Society of Chemistry 2013, Soft Matter, 2013, 9, 5361-5371, Issue 22, RSC Publishing, 11 pages.

* cited by examiner

*Primary Examiner* — Vishal V Vasisth
(74) *Attorney, Agent, or Firm* — Loza & Loza, LLP; Robert Goozner

(57) ABSTRACT

A polymer comprising units having the structure (I):

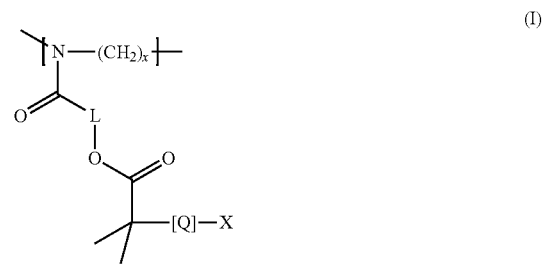

wherein x is 2 or 3, wherein L is $(CH_2)_y$, where y is an integer from 1 to 10, or wherein L is $CH(CH_3)CH_2S(CH_2)_z$, where z is an integer from 1 to 5; wherein [Q] is absent or is a polymerised moiety consisting of units having the structure (II):

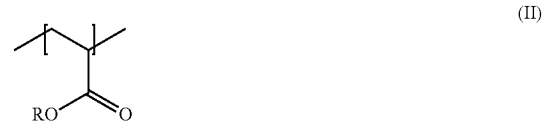

wherein R is a hydrocarbyl group, or a hydrocarbyl group containing one or more heteroatoms, wherein R may be linear, branched or cyclic, saturated or unsaturated, and wherein R has from 1 to 30 carbon atoms; wherein [Q] either consists of identical units of structure (II), or wherein [Q] consists of more than one different units of structure (II), differing in group R; and wherein X is a halogen or another chain terminating group. The polymers may find use as additives in lubricating compositions where they provide friction improvement and wear reduction.

30 Claims, No Drawings

POLYMERS AND LUBRICATING COMPOSITIONS CONTAINING POLYMERS

This invention relates to polymers and in particular to amphiphilic polymers. The invention also relates to lubricating compositions (lubricants) containing the polymers and the use of the polymers as additives for lubricants. Lubricants of particular interest are lubricating oil compositions such as those used to lubricate the crankcase of spark-ignited and compression-ignited internal combustion engines. The polymers provide wear and friction reducing properties to lubricants such as lubricating oil compositions thereby improving efficiency and helping to reduce wear.

There is much interest in improving the fuel economy of gasoline and diesel engines. This can be done, through the lubricant engine oil, by reducing the friction contribution either of the bulk fluid (by lowering the oil viscosity) or reducing friction between the contacting parts by the inclusion of friction modifier additives. There is also an ongoing need to reduce the occurrence of wear in engines.

In a first aspect, the invention provides a polymer comprising units having the structure (I):

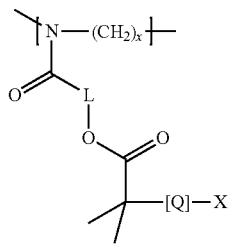

(I)

wherein x is 2 or 3, wherein L is $(CH_2)_y$, where y is an integer from 1 to 10, or wherein L is $CH(CH_3)CH_2S(CH_2)_z$, where z is an integer from 1 to 12, preferably from 1 to 5; wherein [Q] is absent or is a polymerised moiety consisting of units having the structure (II)

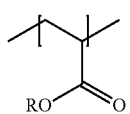

(II)

wherein R is a hydrocarbyl group, or a hydrocarbyl group containing one or more heteroatoms, wherein R may be linear, branched or cyclic, saturated or unsaturated, and wherein R has from 1 to 30 carbon atoms;
wherein [Q] either consists of identical units of structure (II), or wherein [Q] consists of more than one different units of structure (II), differing in group R;
and wherein X is a halogen or another chain terminating group.

Preferably, the number of units of structure (I) in the polymer is from 2 to 100, preferably from 2 to 50, for example from 5 to 30.

In an embodiment, the polymer further comprises units having the structure (III):

(III)

wherein $R^1$ is a linear or branched, saturated or unsaturated hydrocarbyl group having from 1 to 50, preferably from 2 to 24, for example 2 to 18 carbon atoms; and wherein w is 2 or 3.

In an embodiment, the polymer consists of units of structure (I).

In another embodiment, the polymer consists of units of structure (I) and units of structure (III).

The polymer of the present invention will now be described in more detail.

The polymer of the present invention comprises units having the structure (I):

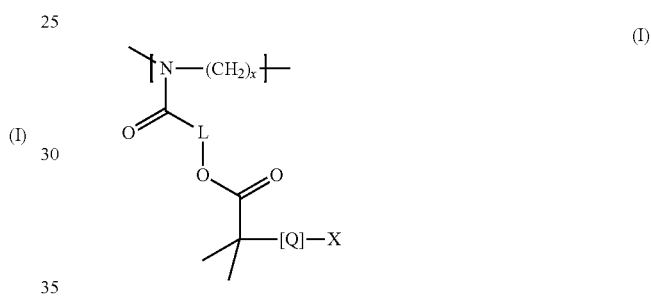

(I)

In an embodiment, all units of structure (I) have the same value of x; either 2 or 3. In an alternative embodiment, in some units x is 2 and in others, x is 3. The ratio of the number of units where x is 2 to the number of units where x is 3 may be any suitable ratio but is preferably from 1:100 to 100:1.

In an embodiment, group L is $(CH_2)_y$ where y is an integer from 1 to 20. Preferably, y is an integer from 1 to 10, more preferably 2 to 7, for example 5.

In another embodiment, group L is $CH(CH_3)CH_2S(CH_2)_z$ where z is an integer from 1 to 12, preferably from 1 to 5. In an embodiment, z is 2.

In an embodiment, [Q] is absent.

In an alternative embodiment, [Q] is a polymerised moiety consisting of units having the structure (II):

(II)

It is to be understood that in the context of the present invention, the polymerised moiety includes moieties which may more strictly be termed 'oligomers'. The number of units of structure (II) present may be a few as 2. Preferably, the number of units of structure (II) in [Q] is from 2 to 200, more preferably 2 to 100, even more preferably 2 to 50.

Preferably, the ratio of the number of units of structure (I) in the polymer to the number of units of structure (II) in the polymerised moiety [Q] is from 1:50 to 50:1, more preferably from 1:20 to 20:1, even more preferably from 1:10 to 10:1, such as from 1:5 to 5:1, 1:2 to 2:1, for example 1:1.

The polymerised moiety [Q] may be homo-polymeric in the sense that it consists of a single type of unit of structure (II). In this case, all groups R in [Q] will be the same.

In another embodiment, the polymerised moiety [Q] may be co-polymeric such that two or more different types of units of structure (II) are present. These different types of units of structure (II) will be distinguished by different groups R. When [Q] is co-polymeric, the different units of structure (II) may be arranged as statistical copolymers which are formed where the polymerisation follows a known statistical rule, for example Bernouillian statistics or Markovian statistics. Alternatively, the different units of structure (II) may be arranged as a random copolymer. Further alternatively, the different units of structure (II) may be arranged in an ordered way to provide alternating copolymers, periodic copolymers or block copolymers. In a particular embodiment, two or more different types of units of structure (II) form a block copolymer.

When [Q] is co-polymeric, different types of units of structure (II), distinguished by different groups R, will be present. The number of different types of units of structure (II) present is not limited but in preferred embodiments, 2, 3, 4, 5 or more, for example up to 12, different types of units of structure (II), each distinguished by a different group R, will be present. In a particularly preferred embodiment 2 different types of units of structure (II) will be present. The proportion of each different type of unit of structure (II) present in [Q] is not limited. In the case where [Q] consists of 2 different types of units of structure (II), the ratio of the number of units of one type to the number of units of another type is preferably in the range from 1:100 to 100:1, more preferably 1:50 to 50:1, even more preferably 1:20 to 20:1, for example 1:10 to 10:1. It will be understood that a polymerised moiety [Q] may consist of only a single unit of structure (II) of one type with a single unit, or two or more, units of structure (II) of another type. For example, in a particular embodiment, [Q] may consist of one unit, preferably 2 or more units, of structure (II) of one type with a single unit of structure (II) of another type terminally attached. This arrangement is illustrated below for a moiety [Q] having three units of structure (II) carrying group R and having a terminal unit of structure (II) carrying group R', where R and R' are different:

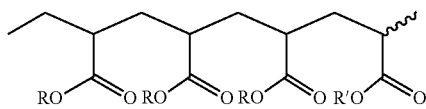

Groups R are hydrocarbyl groups or hydrocarbyl groups containing one or more heteroatoms. As discussed above, all groups R present in [Q] may be identical, that is each unit of structure (II) present will be the same. Alternatively, 2 or more different units of structure (II) may be present, each differing in group R.

Examples of hydrocarbyl groups suitable as group R are linear alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and higher analogues. Also suitable are branched alkyl groups such as iso-propyl, iso-butyl, sec-butyl, tert-butyl, 2-methylpentyl, 2-propylheptyl, 2-butyloctyl, 2-ethylhexyl, iso-octyl, iso-nonyl, 2-tert-butylheptyl, 3-isopropylheptyl, 5-methylundecyl, 2-methyldodecyl, 5-methyltridecyl, 2-methylhexadecyl, 5-isopropylheptadecyl, 4-tert-butyloctadecyl, 5-ethyloctadecyl, 3-isopropyl-octadecyl, and similar.

Further examples of hydrocarbyl groups suitable as group R are linear alkenyl groups such as ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl and higher analogues. As is known in the art, alkenyl groups may contain a single carbon-carbon double bond which may be situated at any point on the carbon chain. So, for example, a propenyl group may be prop-1-enyl or prop-2-enyl. Alkenyl groups may alternatively contain more than one carbon-carbon double bond, an example being a 'di-enyl' group containing two carbon-carbon double bonds. In groups with multiple carbon-carbon double bonds, the double bonds may be conjugated or non-conjugated.

In an embodiment, groups R may be linear alkenyl groups derived from natural sources of fatty acids such as plant oils or those derived from animal fats. Such fatty acids are mixtures of compounds of differing carbon chain lengths and so the groups R derived therefrom are similarly mixed. Often such groups are designated as CX:Y where X refers to the number of carbon atoms in the group and Y is the number of double bonds in the group. An example is the oleyl group (derived from oleic acid) and designated C18:1 which has 18 carbon atoms and a single carbon-carbon double bond. Mixtures predominating in C18:1, C18:2, C18:3 are a suitable example. As is known in the art, mixtures derived from natural fatty acids may also contain, usually minor amounts of, alkyl groups; for example, stearyl (C18:0).

Suitable branched alkenyl groups are the double-bond-containing analogues of the branched alkyl groups described above.

Triple-unsaturated groups, that is alkynyl groups, are also suitable. An example is the propargyl group.

Also suitable as hydrocarbyl groups R are saturated and unsaturated cyclic, including polycyclic, groups. Such groups may be substituted or unsubstituted. Examples of mono-cyclic saturated groups include 6 yclopropyl, cyclobutyl, cyclopentyl, cyclohexyl, cycloheptyl, cyclooctyl, cyclononyl and cyclodecyl. Examples of poly-cyclic saturated groups include those derived from decalin and similar. Examples of unsaturated groups are benzyl, naphthyl and those derived from anthracene, phenanthrene, phenalene and similar.

Substituted analogues of saturated and unsaturated cyclic, including polycyclic, groups may include those substituted by a single alkyl or alkenyl group or by more than one alkyl or alkenyl group or mixture thereof. Substituent groups may be linear or branched and may include those alkyl and alkenyl groups described above.

Alternatively, or additionally, groups R may be hydrocarbyl groups containing one or more heteroatoms. Heteroatoms include oxygen, sulphur, nitrogen, phosphorus and the halogens. As is known in the art, heteroatoms may be situated between saturated or unsaturated carbon-carbon bonds, such as for example those found in ethers or pyridine, or they may be situated in substituent groups attached to hydrocarbyl groups, such as for example hydroxy or carboxylic acid groups. Both of these types of group are considered to be hydrocarbyl groups containing one or more heteroatoms as are groups where there are both one or more heteroatoms situated between saturated or unsaturated carbon-carbon bonds and one or more heteroatoms situated in substituent groups.

An example of a hydrocarbyl group containing one or more heteroatoms is a polyalkylene glycol group of the structure —[(CR$_2$H)$_a$O]$_b$OR$_3$ where a is an integer from 2 to 4, preferably 2, and b is from 2 to 100, preferably 2 to 20, for example from 2 to 10. R$_2$ is hydrogen or an alkyl residue such as CH$_2$ or CH$_2$CH$_2$. Preferably, R$_2$ is hydrogen. R$_3$ is hydrogen, an alkyl group such as methyl or ethyl or an aryl group such as phenyl. Preferably, R$_3$ is methyl. Preferably a is 2 and R$_2$ is hydrogen such that the groups are polyethylene glycol groups. In preferred embodiments, R$_2$ is hydrogen, a is 2 and b is 2 such that the groups are diethylene glycol groups. In other preferred embodiments, a is 2 and b is an average value of 7 to 8 such that the groups are oligoethyleneglycol groups.

A further example of a hydrocarbyl group containing one or more heteroatoms is a group carrying one or more hydroxyl groups. These include for example a hydroxybenzyl group and similar aromatic groups carrying one or more hydroxy groups. Also suitable are amino and silyl groups.

In an embodiment, the polymer further comprises units having the structure (III):

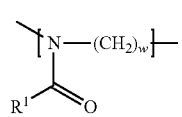

(III)

Preferred as the hydrocarbyl group R$^1$ as those hydrocarbyl groups described hereinabove in relation to hydrocarbyl groups R.

In a preferred embodiment, group R$^1$ comprises a linear alkenyl group, or a mixture of linear alkenyl groups, derived from natural sources of fatty acids such as plant oils or those derived from animal fats. These are described hereinabove in relation to group R.

Preferably, R$^1$ comprises a mixture of linear alkenyl groups, derived from natural sources of fatty acids such as plant oils or those derived from animal fats where at least 10% of the groups comprise unsaturated hydrocarbyl groups having between 8 and 20 carbon atoms. More preferably, at least 20% or 30% or 40% or 50% of the groups R$^1$ comprise unsaturated hydrocarbyl groups having between 8 and 20 carbon atoms. Most preferably, at least 60% or 70% of the groups R$^1$ comprise unsaturated hydrocarbyl groups having between 8 and 20 carbon atoms. Preferably, at least 10% of the groups R$^1$ comprise unsaturated hydrocarbyl groups having between 15 and 20 carbon atoms. More preferably, at least 20% or 30% or 40% or 50% of the groups R comprise unsaturated hydrocarbyl groups having between 15 and 20 carbon atoms. Most preferably, at least 60% or 70% of the groups R$^1$ comprise unsaturated hydrocarbyl groups having between 15 and 20 carbon atoms.

Preferably, R$^1$ comprises a mixture of linear alkenyl groups wherein at least 5% of the groups comprise unsaturated hydrocarbyl groups having 17 carbon atoms. More preferably, at least 10% or 20% or 30% or 40% or 50% or 60% of the groups R$^1$ comprise unsaturated hydrocarbyl groups having 17 carbon atoms. Even more preferably, at least 70% of the groups R$^1$ comprise unsaturated hydrocarbyl groups having 17 carbon atoms.

In preferred embodiments, R$^1$ comprises a mixture of linear alkenyl groups wherein at least at least 50% of the groups comprise single, double or triple-unsaturated C17 alkenyl groups or any mixture thereof. More preferably, at least 60% of the groups R$^1$ comprise single, double or triple-unsaturated CH alkenyl groups or any mixture thereof. Even more preferably, at least 70% of the groups R$^1$ comprise single, double or triple-unsaturated C17 alkenyl groups or any mixture thereof.

In particularly preferred embodiments, groups R$^1$ comprise a mixture of single, double or triple-unsaturated C$_{17}$ alkenyl groups which mixture predominates in single, and double-unsaturated C$_{17}$ alkenyl groups. Such mixtures may comprise small amounts of smaller and longer molecules.

In an embodiment, in all units of structure (II) present, w is 2. In another embodiment, in all units of structure (III) present, w is 3. In yet another embodiment, units of structure (III) present will be a mixture of moieties where w is 2 and those where w is 3, In this embodiment, the ratio of the number of units of structure (III) where w is 2 to the number of units of structure (III) where w is 3 may be any value but is preferably in the range from 1:100 to 100:1, more preferably from 1:50 to 50:1 or 1:20 to 20:1, for example from 1:10 to 10:1.

When the polymer of the invention comprises, or consists of, units of structure (1) and units of structure (III), the units of structures (I) and (III) may be may be arranged as statistical copolymers which are formed where the polymerisation follows a known statistical rule, for example Bernouillian statistics or Markovian statistics. Alternatively, the units of structures (I) and (III) may be arranged as a random copolymer. Further alternatively, the units of structures (I) and (III) may be arranged in an ordered way to provide alternating copolymers, periodic copolymers or block copolymers.

Preferably, when the polymer of the invention comprises, or consists of, units of structure (I) and units of structure (III), the ratio of the number of units of structure (I) to the number of units of structure (III) is from 1:100 to 100:1, more preferably from 1:50 to 50:1 or 1:20 to 20:1, for example from 1:10 to 10:1.

In the polymers of the invention X is a halogen or a chain terminating group. Preferably, X is a halogen, and most preferably, X is bromine. As is known in the art, end group transformation reactions can be used to provide chain terminating groups X of various types. For example, X may be a hydroxy group, an azide group, NH$_2$ thioether group or ether group.

The polymers of the invention may be of any molecular weight but preferably have a number average molecular weight (Mn) of between 500 and 500,000 g/mol, preferably 1,000 to 250,000 g/mol, more preferably 5,000 to 100,000 g/mol, for example 10,000 to 50,000 g/mol, as measured by Gel Permeation Chromatography with reference to linear, narrow poly(methylmethacrylate) standards in the range of 500 to 600,000 g/mol.

Particular examples of polymers according to the invention include a polymer having 10 units of structure (I) and where [Q] consists of 20 units of structure (II) where each group R is 2-ethylhexyl; a polymer having 50 units of structure (I) and where [Q] consists of 5 units of structure (II) where each group R is 2-ethylhexyl; and a polymer having 10 units of structure (I) and where [Q] consists of 10 units of structure (II) where each group R is 2-ethylhexyl. Other examples include a polymer having 10 units of structure (I) and where [Q] consists of 10 units of structure (II) where each group R is 2-ethylhexyl and a single terminal unit of structure (II) where R is a catechol group; and a polymer having 10 units of structure (I) and where [Q]

consists of a random copolymer of 10 units of structure (II) where each group R is 2-ethylhexyl and 5 units of structure (II) where each group R is heptadecylethyleneglycol methyl ether. In all cases, L may be $(CH_2)_y$ or $CH(CH_3)CH_2S(CH_2)_2$ where y and z are as defined above.

Methods for synthesising polymers according to the present invention will now be described.

As in initial step, a compound of structure:

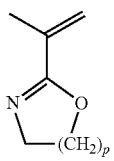

where p is either 1 (2-isopropenyl-2-oxazoline) or 2 (2-isopropenyl-5,6-dihydro-4H-1,3-oxazine) is reacted with a mercaptoalcohol, e.g. 2-mercaptoethanol in this example, to form a structure:

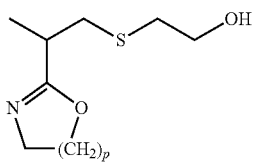

It will be understood that the carbon chain between the sulphur atom and the terminal hydroxyl group is determined by the size of the mercaptoalcohol used. Although shown above for 2-mercaptoethanol, analogous mercaptoalcohols with longer carbon chains are equally suitable.

A Steglich esterification reaction is then performed where the compound above is further reacted with a tertiary halo-acid, for example α-bromoisobutyric acid, in the presence of 4-N,N-dimethylaminopyridine and a dihydrocarbyldiimide, for example, N,N'-diisopropylcarbodiimide, to form a compound (Compound A) of the structure:

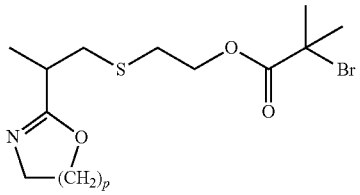

Compound A

In an alternative initial step, a lactone is first ring-opened by reacting with an 2-amino-1-ethanol or 3-amino-1-propanol, via nucleophilic attack of the nitrogen lone pair. For example, caprolactone ring-opened using 2-amino-1-ethanol produces the structure:

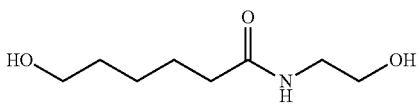 [SMILES: O=C(CCCCCO)NCCO]

This compound is then ring-closed via an organometallic-catalysed condensation-cyclisation reaction by heating in the presence of transition metal catalyst, e.g. $Ti(OnBu)_4$, to form:

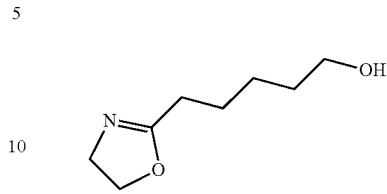

As before, a Steglich esterification reaction is then performed where the compound above is further reacted with a tertiary halo-acid, for example α-bromoisobutyric acid, in the presence of 4-N,N-dimethylaminopyridine and a dihydrocarbyldiimide, for example, N,N'-diisopropylcarbodiimide, to form a compound (Compound B) of the structure:

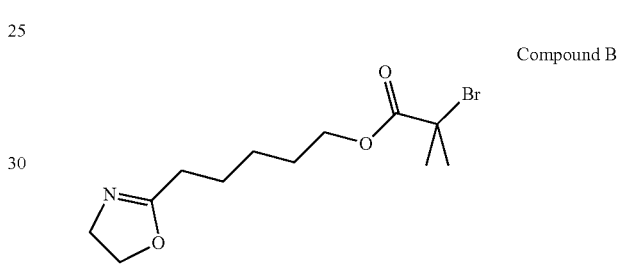

Compound B

It will be understood that the same reaction replacing 2-amino-1-ethanol with 3-amino-1-propanol in the ring-opening reaction will produce a compound (Compound B') of the structure:

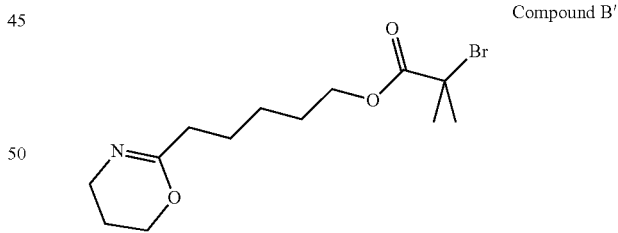

Compound B'

It will also be understood that the length of the carbon chain between the ring moiety and the in-chain oxygen atom is determined by the size of the lactone used in the ring-opening reaction. As is known in the art, lactones both larger and smaller than caprolactone are available and suitable for use in the present invention.

Compounds A, B and B', or their analogues, are used as monomers in polymerisation reaction to form polymers according to the invention.

Polymerisation of Compounds A, B and B', or their analogues, absent other monomers, produces polymers having units of structure (I) only, where [Q] is absent.

Alternatively, co-polymerisation of Compounds A, B and B', or their analogues with:

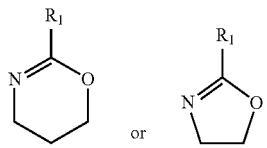

or a mixture thereof, where R, is as defined above in relation to structure (III), produces polymers having units of structure (I), where [Q] is absent, and also units of structure (III). Polymerisation can be achieved using cationic ring-opening polymerisation (CROP). A suitable synthetic route involves heating the monomer, or mixture of monomers in the presence of a tosylate, e.g. methyl tosylate, a triflate, a primary or secondary alkyl bromide or iodide, or a Lewis acid.

Polymerised moieties [Q] can be introduced by reacting a polymer formed as above with one or more acrylate monomers. This is suitably achieved using Cu(0)-mediated Reversible-Deactivation radical Polymerisation (RDRP) where the initial polymer acts as the initiator. A de-activator (e.g. CuBr) and a ligand (e.g. Me$_6$TREN) are used. If a single acrylate is used, then [Q] consists of units of structure (II) where all groups R are the same. Using a mixture of 2 or more different acrylate monomers results in a moiety [Q] where units of structure (II) with different groups R are randomly arranged. Alternatively, the reaction may be undertaken in two or more stages, the first stage producing units of structure (II) where groups R are of one type and then by subsequent addition of a different acrylate monomer, units of structure (II) where groups R are of a different type. In this way, moieties [Q] have a block co-polymer architecture where the size of each block can be controlled by controlling the amount of each acrylate monomer used.

Compounds A, B and B', and their analogues, and their synthesis, form other aspects of the present invention and so in another aspect, the present invention provides a compound of structure (IV):

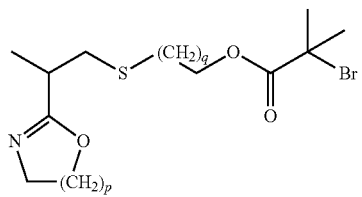

where p is 1 or 2, and where q is an integer from 1 to 10, preferably from 1 to 5.

In another aspect, the present invention provides a compound of structure (V):

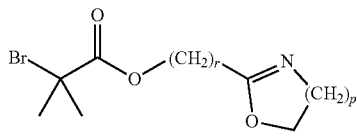

where p is 1 or 2, and where r is an integer from 4 to 10, preferably from 2 to 5.

In another aspect, the present invention provides a method for synthesising a compound of structure (IV), the method comprising:
(a) reacting 2-isopropenyl-2-oxazoline, 2-isopropenyl-5,6-dihydro-4H-1,3-oxazine or a mixture thereof, with a mercapto alcohol;
(b) performing a Steglich esterification reaction by reacting the product of step (a) with α-bromoisobutyric acid, in the presence of 4-N,N-dimethylaminopyridine and a dihydrocarbyldiimide, preferably N,N'-diisopropylcarbodiimide.

In another aspect, the present invention provides a method for synthesising a compound of structure (V), the method comprising:
(a) ring-opening a lactone via reaction with 2-amino-1-ethanol, 3-amino-1-propanol, or a mixture thereof;
(b) ring-closing the product of step (a) via an organometallic-catalysed condensation-cyclisation reaction by heating in the presence of transition metal catalyst, preferably Ti(OnBu)$_4$;
© performing a Steglich esterification reaction by reacting the product of step (b) with a α-bromoisobutyric acid, in the presence of 4-N,N-dimethylaminopyridine and a dihydrocarbyldiimide, preferably N,N'-diisopropylcarbodiimide.

In this specification, the following words and expressions, if and when used, have the meaning given below:
"active ingredients" or "(a.i.)" refers to additive material that is not diluent or solvent;
"comprising" or any cognate word specifies the presence of stated features, steps, or integers or components, but does not preclude the presence or addition of one or more other features, steps, integers, components or groups thereof. The expressions "consists of" or "consists essentially of" or cognates may be embraced within "comprises" or any cognate word. The expression "consists essentially of" permits inclusion of substances not materially affecting the characteristics of the composition to which it applies. The expression "consists of" or cognates means only the stated features, steps, integers components or groups thereof are present to which the expression refers;
"oil-soluble" or "oil-dispersible", or cognate terms, used herein do not necessarily indicate that the compounds or additives are soluble, dissolvable, miscible, or are capable of being suspended in an oil in all proportions. These do mean, however, that they are, for example, soluble or stably dispersible in oil to an extent sufficient to exert their intended effect in the environment in which the oil is employed. Moreover, the additional incorporation of other additives may also permit incorporation of higher levels of a particular additive, if desired;
"ashless" in relation to an additive means the additive does not include a metal;
"ash-containing" in relation to an additive means the additive includes a metal;
"major amount" means in excess of 50 mass % of a composition or mixture;
"minor amount" means 50 mass % or less of a composition or mixture;
"effective amount" in respect of an additive means an amount of such an additive in the composition (e.g. an additive concentrate) that is effective to provide, and provides, the desired technical effect;
"ppm" means parts per million by mass, based on the total mass of a composition;

"metal content" of a composition or of an additive component, for example molybdenum content or total metal content of the additive concentrate (i.e. the sum of all individual metal contents), is measured by ASTM D5185;

"TBN" in relation to an additive component or of a composition, means total base number (mg KOH/g) as measured by ASTM D2896;

"$KV_{100}$" means kinematic viscosity at 100° C. as measured by ASTM D445;

HTHS means High Temperature High Shear at 150° C. as measured by—CEC-L-36-A 90.

"phosphorus content" is measured by ASTM D5185;

"sulfur content" is measured by ASTM D2622;

"sulfated ash content" is measured by ASTM D874;

"$M_n$" means number average molecular weight as measured by Gel Permeation Chromatography with reference to linear narrow poly(methylmethacrylate) standards in the range of 550 to 600,000 g/mol;

"$M_w$" means weight average molecular weight as measured by Gel Permeation Chromatography with reference to linear narrow poly(methylmethacrylate) standards in the range of 550 to 600,000 g/mol;

"dispersity" means $M_w/M_n$, (denoted by D).

Also, it will be understood that various components used, essential as well as optimal and customary, may react under condition of formulation, storage and use and that the invention also provides the product(s) obtainable or obtained by any such reaction.

Further it is understood that any upper and lower quality, range or ratio limits set forth herein may be independently combined.

Lubricating Compositions

In a second aspect, the present invention provides a lubricating composition comprising a major amount of more than 50 percent by mass, based on the mass of the composition, of a base lubricant and a minor amount of less than 50 percent by mass, based on the mass of the composition, of a polymer according to the first aspect of the invention. The polymers provide friction reducing properties to lubricants. The use of such lubricants to lubricate machines such as engines, transmissions, gears and the like thus improve the efficiency of the machine and helps to reduce wear of contacting machine parts.

The base lubricant may be a lubricating oil, a grease or a fuel oil. In a preferred embodiment, the base lubricant is a lubricating oil such that the lubricating composition is a lubricating oil composition.

Lubricating oil compositions of the invention may be for example, lubricants suitable for use as motor vehicle motor oils and comprise a major amount of oil of lubricating viscosity and a minor amount of a polymer according to the first aspect of the invention. Typically, lubricating oil compositions will also contain other performance-enhancing additives (co-additives), in addition to the polymer. The lubricating composition may also be in the form of an additive concentrate for blending with oil of lubricating viscosity to make a final lubricant.

The lubricating oil compositions of the invention will preferably contain 0.01 to 10 percent by mass, based on the mass of the composition of the polymer of the present invention, more preferably 0.01 to 5, for example up to 0.5, 1, 2, 3 or 4 percent by mass, based on the mass of the composition. When in the form of an additive concentrate, typically the polymer will be present in an oil of lubricating viscosity, or other suitable carrier fluid, in an amount of 0.07 to 70 percent by mass, based on the mass of the composition.

The oil of lubricating viscosity (sometimes referred to as "base stock" or "base oil") is the primary liquid constituent of a lubricant, into which additives and possibly other oils are blended, for example to produce a final lubricant (or lubricant composition). A base oil, which is useful for making additive concentrates as well as for making lubricating oil compositions therefrom, may be selected from natural oils (vegetable, animal or mineral) and synthetic lubricating oils and mixtures thereof.

Definitions for the base stocks and base oils in this invention are the same as those found in the American Petroleum Institute (API) publication "Engine Oil Licensing and Certification System", Industry Services Department, Fourteenth Edition, December 1996, Addendum 1, December 1998, which categorizes base stocks as follows:

a) Group I base stocks contain less than 90 percent saturates and/or greater than 0.03 percent sulphur and have a viscosity index greater than or equal to 80 and less than 120 using the test methods specified in Table E-1.

b) Group II base stocks contain greater than or equal to 90 percent saturates and less than or equal to 0.03 percent sulphur and have a viscosity index greater than or equal to 80 and less than 120 using the test methods specified in Table E-1.

c) Group III base stocks contain greater than or equal to 90 percent saturates and less than or equal to 0.03 percent sulphur and have a viscosity index greater than or equal to 120 using the test methods specified in Table E-1.

d) Group IV base stocks are polyalphaolefins (PAO).

e) Group V base stocks include all other base stocks not included in Group I, II, III, or IV.

Typically, the base stock has a viscosity preferably of 3-12, more preferably 4-10, most preferably 4.5-8, mm²/s at 100° C.

TABLE E-1

Analytical Methods for Base Stock

| Property | Test Method |
|---|---|
| Saturates | ASTM D 2007 |
| Viscosity Index | ASTM D 2270 |
| Sulphur | ASTM D 2622 |
|  | ASTM D 4294 |
|  | ASTM D 4927 |
|  | ASTM D 3120 |

Preferably, the oil of lubricating viscosity comprises greater than or equal to 10, more preferably greater than or equal to 20, even more preferably greater than or equal to 25, even more preferably greater than or equal to 30, even more preferably greater than or equal to 40, even more preferably greater than or equal to 45, mass % of a Group II or Group III base stock, based on the total mass of the oil of lubricating viscosity. Even more preferably, the oil of lubricating viscosity comprises greater than 50, preferably greater than or equal to 60, more preferably greater than or equal to 70, even more preferably greater than or equal to 80, even more preferably greater than or equal to 90, mass % of a Group II or Group III base stock, based on the total mass of the oil of lubricating viscosity. Most preferably, the oil of lubricating viscosity consists essentially of a Group II and/or Group III base stock. In some embodiments the oil of lubricating viscosity consists solely of Group II and/or Group III base stock. In the latter case it is acknowledged that additives included in the lubricating oil composition may comprise a carrier oil which is not a Group II or Group III base stock.

Other oils of lubricating viscosity that may be included in the lubricating oil composition are detailed as follows:

Natural oils include animal and vegetable oils (e.g. castor and lard oil), liquid petroleum oils and hydro refined, solvent-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils such as polymerized and interpolymerized olefins (e.g. polybutylenes, polypropylenes, propylene-isobutylene copolymers, chlorinated polybutylenes, poly(1-hexenes), poly(1-octenes), poly(1-decenes)); alkylbenzenes (e.g. dodecylbenzenes, tetradecylbenzenes, dinonylbenzenes, di(2-ethylhexyl)benzenes); polyphenols (e.g. biphenyls, terphenyls, alkylated polyphenols); and alkylated diphenyl ethers and alkylated diphenyl 19 ulphides and the derivatives, analogues and homologues thereof.

Another suitable class of synthetic lubricating oil comprises the esters of dicarboxylic acids (e.g. phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g. butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebasic acid with two moles of tetraethylene glycol and two moles of 2-ethylhexanoic acid.

Esters useful as synthetic oils also include those made from $C_5$ to $C_{12}$ monocarboxylic acids and polyols, and polyol ethers such as neopentyl glycol, trimethylolpropane, pentaerythritol, dipentaerythritol and tripentaerythritol.

Unrefined, refined and re-refined oils can be used in the compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be unrefined oil. Refined oils are similar to the unrefined oils except they have been further treated in one or more purification steps to improve one or more properties. Many such purification techniques, such as distillation, solvent extraction, acid or base extraction, filtration and percolation, are known to those skilled in the art. Re-refined oils are obtained by processes similar to those used to obtain refined oils applied to refined oils that have been already used in service. Such re-refined oils are also known as reclaimed or reprocessed oils and often are additionally processed by techniques for treating spent additive and oil breakdown products.

Other examples of base oil are gas-to-liquid ("GTL") base oils, i.e. the base oil may be an oil derived from Fischer-Tropsch synthesised hydrocarbons made from synthesis gas containing H2 and CO using a Fischer-Tropsch catalyst. These hydrocarbons typically require further processing in order to be useful as a base oil. For example, they may, by methods known in the art, be hydroisomerized; hydrocracked and hydroisomerized; dewaxed; or hydroisomerized and dewaxed.

The oil of lubricating viscosity may also comprise a Group I, Group IV or Group V base stocks or base oil blends of the aforementioned base stocks.

The lubricating compositions of the present invention preferably comprise at least 60% by weight, for example 70% by weight or more of an oil of lubricating viscosity, based on the weight of the composition.

Co-Additives

The lubricating compositions, particularly lubricating oil compositions, of the present invention may further comprise one or more phosphorus-containing compounds; oxidation inhibitors or anti-oxidants; dispersants; metal detergents; anti-wear agents; friction modifiers, viscosity modifiers and other co-additives, provided they are different from the polymer of the present invention. These will be discussed in more detail below.

Suitable phosphorus-containing compounds include dihydrocarbyl dithiophosphate metal salts, which are frequently used as antiwear and antioxidant agents. The metal is preferably zinc, but may be an alkali or alkaline earth metal, or 20 luminium, lead, tin, molybdenum, manganese, nickel or copper. The zinc salts are most commonly used in lubricating oil in amounts of 0.1 to 10, preferably 0.2 to 2 mass %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$, and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil-soluble salts of dihydrocarbyl dithiophosphoric acids and may be represented by the following formula:

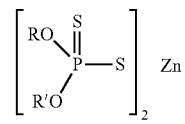

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be 5 or greater. The zinc dihydrocarbyl dithiophosphate (ZDDP) can therefore comprise zinc dialkyl dithiophosphates. Lubricating oil compositions of the present invention suitably may have a phosphorus content of no greater than about 0.08 mass % (800 ppm). Preferably, in the practice of the present invention, ZDDP is used in an amount close or equal to the maximum amount allowed, preferably in an amount that provides a phosphorus content within 100 ppm of the maximum allowable amount of phosphorus. Thus, lubricating oil compositions useful in the practice of the present invention preferably contain ZDDP or other zinc-phosphorus compounds, in an amount introducing from 0.01 to 0.08 mass % of phosphorus, such as from 0.04 to 0.08 mass % of phosphorus, preferably, from 0.05 to 0.08 mass % of phosphorus, based on the total mass of the lubricating oil composition.

Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol 22 ulphide, oil soluble phenates and sulfurized phenates, phosphosulfuarized or sulfurized hydrocarbons or esters, phosphorous esters, metal thiocarbamates, oil soluble copper compounds as described in U.S. Pat. No. 4,867,890, and molybdenum-containing compounds.

Aromatic amines having at least two aromatic groups attached directly to the nitrogen constitute another class of compounds that is frequently used for antioxidancy. Typical oil-soluble aromatic amines having at least two aromatic groups attached to directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —$SO_2$— or alkylene group) and two are directly attached to one amine nitrogen are also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups. The amount of any such oil soluble aromatic amines having at least two aromatic groups attached directly to one amine nitrogen should preferably not exceed 0.4 mass %.

A dispersant is an additive whose primary function is to hold solid and liquid contaminations in suspension, thereby passivating them and reducing engine deposits at the same time as reducing sludge depositions. For example, a dispersant maintains in suspension oil-insoluble substances that result from oxidation during use of the lubricant, thus preventing sludge flocculation and precipitation or deposition on metal parts of the engine.

Dispersants in this invention are preferably "ashless", as mentioned above, being non-metallic organic materials that form substantially no ash on combustion, in contrast to metal-containing and hence ash-forming materials. They comprise a long hydrocarbon chain with a polar head, the polarity being derived from inclusion of e.g. an O, P, or N atom. The hydrocarbon is an oleophilic group that confers oil-solubility, having, for example 40 to 500 carbon atoms. Thus, ashless dispersants may comprise an oil-soluble polymeric backbone.

A preferred class of olefin polymers is constituted by polybutenes, specifically polyisobutenes (PIB) or poly-n-butenes, such as may be prepared by polymerization of a $C_4$ refinery stream.

Dispersants include, for example, derivatives of long chain hydrocarbon-substituted carboxylic acids, examples being derivatives of high molecular weight hydrocarbyl-substituted succinic acid. A noteworthy group of dispersants is constituted by hydrocarbon-substituted succinimides, made, for example, by reacting the above acids (or derivatives) with a nitrogen-containing compound, advantageously a polyalkylene polyamine, such as a polyethylene polyamine. Particularly preferred are the reaction products of polyalkylene polyamines with alkenyl succinic anhydrides, such as described in U.S. Pat. Nos. 3,202,678; 3,154,560; 3,172,892; 3,024,195; 3,024,237, 3,219,666; and 3,216,936, that may be post-treated to improve their properties, such as borated (as described in U.S. Pat. Nos. 3,087,936 and 3,254,025), fluorinated or oxylated. For example, boration may be accomplished by treating an acyl nitrogen-containing dispersant with a boron compound selected from boron oxide, boron halides, boron acids and esters of boron acids.

Preferably, the dispersant, if present, is a succinimide-dispersant derived from a polyisobutene of number average molecular weight in the range of 1000 to 3000, preferably 1500 to 2500, and of moderate functionality. The succinimide is preferably derived from highly reactive polyisobutene.

Another example of dispersant type that may be used is a linked aromatic compound such as described in EP-A-2 090 642.

A detergent is an additive that reduces formation of piston deposits, for example high-temperature varnish and lacquer deposits in engines; it normally has acid-neutralising properties and is capable of keeping finely divided solids in suspension. Most detergents are based on metal "soaps", that is metal salts of acidic organic compounds.

Detergents generally comprise a polar head with a long hydrophobic tail, the polar head comprising the metal salt of the acidic organic compound. The salts may contain a substantially stoichiometric amount of the metal when they are usually described as normal or neutral salts and would typically have a total base number or TBN at 100% active mass (as may be measured by ASTM D2896) of from 0 to 80. Large amounts of a metal base can be included by reaction of an excess of a metal compound, such as an oxide or hydroxide, with an acidic gas such as carbon dioxide.

The resulting overbased detergent comprises neutralised detergent as an outer layer of a metal base (e.g. carbonate) micelle. Such overbased detergents may have a TBN at 100% active mass of 150 or greater, and typically of from 200 to 500 or more.

Suitably, detergents that may be used include oil-soluble neutral and overbased sulfonates, phenates, sulfurised phenates, thiophosphonates, salicylates and naphthenates and other oil-soluble carboxylates of a metal, particularly alkali metal or alkaline earth metals, e.g. Na, K, Li, Ca and Mg. The most commonly used metals are Ca and Mg, which may both be present in detergents used in lubricating compositions, and mixtures of Ca and/or Mg with Na, Detergents may be used in various combinations.

Additional additives may be incorporated into the compositions of the invention to enable particular performance requirements to be met. Examples of such additives which may be included in the lubricating oil compositions of the present invention are metal rust inhibitors, viscosity index improvers, corrosion inhibitors, oxidation inhibitors, other friction modifiers, anti-foaming agents, anti-wear agents and pour point depressants. Some are discussed in further detail below.

Friction modifiers and fuel economy agents that are compatible with the other ingredients of the final oil may also be included. Examples of such materials include glyceryl monoesters of higher fatty acids, for example, glyceryl mono-oleate; esters of long chain polycarboxylic acids with diols, for example, the butane diol ester of a dimerized unsaturated fatty acid; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil-soluble organo-molybdenum compounds include dithiocarbamates, dithiophosphates, dithiophosphinates, xanthates, thioxanthates, sulphides, and the like, and mixtures thereof. Particularly preferred are molybdenum dithiocarbamates, dialkyldithiophosphates, alkyl xanthates and alkylthioxanthates.

Additionally, the molybdenum compound may be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkali metal molybdates and other molybdenum salts, e.g., hydrogen sodium molybdate, $MoOCl_4$, $MoO_2Br_2$, $Mo_2O_3Cl_6$, molybdenum trioxide or similar acidic molybdenum compounds.

Among the molybdenum compounds useful in the compositions of this invention are organo-molybdenum compounds of the formulae:

$Mo(R''OCS_2)_4$ and

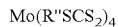

$Mo(R''SCS_2)_4$ wherein R'' is an organo group selected from the group consisting of alkyl, aryl, aralkyl and alkoxyalkyl, generally of from 1 to 30 carbon atoms, and preferably 2 to 12 carbon atoms and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $Mo_3S_kA_nD_z$ and mixtures thereof wherein the A are independently selected ligands having organo groups with a sufficient number of carbon atoms to render the compound soluble or dispersible in the oil, n is from to 4, k varies from 4 to 7, D is selected from the group of neutral electron donating compounds such as water, amines, alcohols, phosphines, and ethers, and z ranges from 0 to 5 and includes non-stoichiometric values. At least 21 carbon atoms should be present among all the ligand organo groups, such as at least 25, at least 30, or at least 35, carbon atoms.

Lubricating oil compositions useful in all aspects of the present invention preferably contain at least 10 ppm, at least 30 ppm, at least 40 ppm and more preferably at least 50 ppm molybdenum. Suitably, lubricating oil compositions useful in all aspects of the present invention contain no more than 1000 ppm, no more than 750 ppm or no more than 500 ppm of molybdenum. Lubricating oil compositions useful in all aspects of the present invention preferably contain from 10 to 1000, such as 30 to 750 or 40 to 500, ppm of molybdenum (measured as atoms of molybdenum).

The viscosity index of the base stock is increased, or improved, by incorporating therein certain polymeric materials that function as viscosity modifiers (VM) or viscosity index improvers (VII). Generally, polymeric materials useful as viscosity modifiers are those having number average molecular weights (Mn) of from 5,000 to 250,000, preferably from 15,000 to 200,000, more preferably from 20,000 to 150,000. These viscosity modifiers can be grafted with grafting materials such as, for example, maleic anhydride, and the grafted material can be reacted with, for example, amines, amides, nitrogen-containing heterocyclic compounds or alcohol, to form multifunctional viscosity modifiers (dispersant-viscosity modifiers).

Polymers prepared with diolefins will contain ethylenic unsaturation, and such polymers are preferably hydrogenated. When the polymer is hydrogenated, the hydrogenation may be accomplished using any of the techniques known in the prior art. For example, the hydrogenation may be accomplished such that both ethylenic and aromatic unsaturation is converted (saturated) using methods such as those taught, for example, in U.S. Pat. Nos. 3,113,986 and 3,700,633 or the hydrogenation may be accomplished selectively such that a significant portion of the ethylenic unsaturation is converted while little or no aromatic unsaturation is converted as taught, for example, in U.S. Pat. Nos. 3,634,595; 3,670,054; 3,700,633 and Re 27,145. Any of these methods can also be used to hydrogenate polymers containing only ethylenic unsaturation and which are free of aromatic unsaturation.

Pour point depressants (PPD), otherwise known as lube oil flow improvers (LOFIs) lower the lowest temperature at which the lube flows. Compared to VM, LOFIs generally have a lower number average molecular weight. Like VM, LOFIs can be grafted with grafting materials such as, for example, maleic anhydride, and the grafted material can be reacted with, for example, amines, amides, nitrogen-containing heterocyclic compounds or alcohol, to form multifunctional additives.

When lubricating compositions contain one or more of the above-mentioned additives, each additive is typically blended into the base oil in an amount that enables the additive to provide its desired function. Representative effective amounts of such additives, when used in crankcase lubricants, are listed below. All the values listed (with the exception of detergent values since the detergents are used in the form of colloidal dispersants in an oil) are stated as mass percent active ingredient (A.I.).

| ADDITIVE | MASS % (Broad) | MASS % (Preferred) |
|---|---|---|
| Dispersant | 0.1-20 | 1-8 |
| Metal Detergents | 0.1-15 | 0.2-9 |
| Corrosion Inhibitor | 0-5 | 0-1.5 |
| Metal dihydrocarbyl dithiophosphate | 0.1-6 | 0.1-4 |
| Antioxidant | 0-5 | 0.01-2.5 |
| Pour Point Depressant | 0.01-5 | 0.01-1.5 |
| Antifoaming Agent | 0-5 | 0.001-0.15 |
| Supplemental Antiwear Agents | 0-1.0 | 0-0.5 |
| Friction Modifier | 0-5 | 0-1.5 |
| Viscosity Modifier | 0.01-10 | 0.25-3 |
| Base stock | Balance | Balance |

Preferably, the Noack volatility of the fully formulated lubricating oil composition (oil of lubricating viscosity plus all additives) is no greater than 18, such as no greater than 14, preferably no greater than 10, mass %. Lubricating oil compositions useful in the practice of the present invention may have an overall sulfated ash content of from 0.5 to 2.0, such as from 0.7 to 1.4, preferably from 0.6 to 1.2, mass %.

It may be desirable, although not essential, to prepare one or more additive concentrates comprising additives (concentrates sometimes being referred to as additive packages) whereby several additives can be added simultaneously to the oil to form the lubricating oil composition.

In another aspect, the present invention provides a method of reducing the friction and/or wear between contacting surfaces of a mechanical device, the method comprising lubricating the surfaces with the lubricating composition of the second aspect. Preferably, the mechanical device is a spark-ignited or compression ignited internal combustion engine.

In another aspect, the present invention provides the use of a polymer according to the first aspect as an additive in a lubricating composition to reduce the friction and/or wear between the contacting surfaces of a mechanical device which is lubricated by the composition. Preferably the lubricating composition is a lubricating oil composition. Preferably, the mechanical device is a spark-ignited or compression ignited internal combustion engine.

EXAMPLES

Example Synthesis of Polymers According to the Invention

As a first stage, 2-isopropenyl-2-oxazoline (5.06 g, 44.09 mmol) and 2-mercaptoethanol (3.2 ml, 44.99 mmol) were stirred in a round-bottom flask for 15 minutes under an inert atmosphere. The reaction mixture was then diluted with anhydrous dichloromethane before addition of 4-(dimethylamino) pyridine (DMAP, 5.54 g, 0.45 mmol) and ca-bromoisobutyric acid (7.50 g, 44.99 mmol). The solution was then cooled in an ice bath and N,N'-diisopropylcarbodiimide (6.97 ml, 44.99 mmol) was slowly added dropwise and the mixture left to stir over-night. Following filtering, washing and solvent removal, and purification by flash chromatography, a colourless oil was obtained (6.67 g, 43.8% yield).

As a second stage, the product obtained in the first stage was combined with p-toluenesulfonic acid, sealed into a microwave vial and purged with nitrogen. Dry acetonitrile was then added to the mixture to form a 4M solution and the vial was re-sealed. The mixture was heated to 60° C. and stirred until full conversion, confirmed by GPC and $^1$H NMR.

As a final stage, the product of the second stage was combined with 2-ethylhexyl acrylate, deactivator (Cu$_2$Br) and ligand (Me$_6$TREN) in a the desired ratios. This mixture was combined with isopropanol (50 wt %) and the resultant solution purged under an inert atmosphere for 30 minutes. Pre-activated copper wire, wound round a magnetic stirrer was added to the reaction vessel. The reaction vessel was placed in an oil bath at 25° C. and left to stir until full conversion.

Test Data

Polymers having the general structure shown below were prepared as described above, varying reactant ratios to give the desired values of n and m.

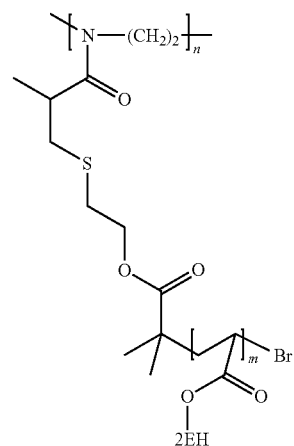

Details of the polymers are shown in the table below.

|  | n | m | n:m | Mn (g/mol) |
|---|---|---|---|---|
| Polymer 1 | 20 | 15 | 1.33 | 33700 |
| Polymer 2 | 10 | 5 | 2 | 10700 |
| Polymer 3 | 50 | 5 | 10 | 21500 |

'2EH' represents a 2-ethylhexyl group.

1 g of each polymer was added to 99 g of an API Group I mineral oil. These samples were subjected to traction and wear testing together with a sample of the same mineral oil without the addition of any polymer.

Each oil was tested using a High Frequency Reciprocating Rig (HFRR) available from PCS Instruments, London, UK. This machine employs a 6 mm diameter ball as an upper specimen which is reciprocated under an applied load against a lower specimen in the form of a disc. The ball and disc are made AISI 52100 polished steel. The test conditions are given in the table below:

| Oil temperature | 140° C. |
|---|---|
| Reciprocating frequency | 40 Hz |
| Stroke length | 1 mm |
| Applied load | 400 g |
| Contact pressure | 1 GPa |
| Test duration | 45 minutes |

The wear scars formed on the lower disc specimens were analysed using a Zemetrics ZeScope 3D optical profilometer using non-contact interferometric focal scanning. This permitted a measurement of the amount of wear by determining the material lost from the disc during the test. This was reported as a wear scar volume (WSV) in units of µm$^3$. The HFRR machine is equipped with a piezoelectric transducer which gives a measurement of the average co-efficient of friction between the ball and the disc. Wear results are shown in the table below where each value is the average of three tests using each test oil.

| Test Oil | WSV/µm$^3$ | Friction co-efficient |
|---|---|---|
| Base oil (no polymer) | 323000 | 0.158 |
| Polymer 1 | 273000 | 0.129 |
| Polymer 2 | 145000 | 0.128 |
| Polymer 3 | 187000 | 0.123 |

It is clear that the polymers of the invention led to a significant reduction in the amount of wear measured on the test samples compared to the base oil alone. These data confirm that the polymers were effective anti-wear agents.

The friction data give an indication of the mechanism of wear protection which is provided by the polymers of the invention. In all cases, the presence of the polymers led to a marked decrease in recorded friction indicating a greater separation of the contacting surfaces.

Further Example Synthesis of Polymers According to the Invention

Synthesis of caprolactone derived hydroxyl oxazoline: ε-caprolactone (30.01 g, 262.84 mmol) was added to a flask and heated to 80° C. under inert conditions. Ethanolamine (17.45 mL, 262.84 mmol) was then added to the flask and subsequently heated at 120° C. for 2 hr. Titanium (IV) butoxide (0.5 mL) was then added to the reaction mixture and heated at 230° C. for 2 hr. The reaction mixture was then distilled in vacuo to obtain s-hydroxy-pentyl oxazoline as a clear yellow oil (7.53 g, 18.2%).

Synthesis of inimer: ε-hydroxy-pentyl oxazoline (5.50 g, 35.00 mmol) was placed in a round bottom flask with DCM. To this mixture, 4-(dimethylamino) pyridine (DMAP, 0.44 g, 3.50 mmol) and α-bromoisobutyric acid (5.89 g, 35.00 mmol). The solution was then cooled to in an ice bath and N,N'-diisopropylcarbodiimide (5.5 mL, 35.00 mol) was slowly added dropwise and left to stir overnight. The urea byproduct was then filtered off and the crude was washed with saturated NaHCO$_3$ and brine. The solvent was then removed in vacuo and the product was purified by flash chromatography (silica gel, EA, TEA 2%) to obtain the inimer as a colourless oil (6.74 g, 62.9%).

General procedure for Cationic Ring Opening Polymerisation (CROP): Monomer, p-toluenesulfonic acid (in appropriate molar ratios) were sealed into microwave vial and purged with N$_2$ for several minutes. Dry acetonitrile was then added to the reaction mixture to form a 4 M solution and the vial was resealed. The reaction mixture was then left to stir at 60° C. until full or near full conversion, which was confirmed by GPC and $^1$H NMR.

General procedure for the synthesis of brush polymers via Cu(0)-RDRP with chain extension: The acrylate monomer, brush initiator, deactivator (Cu$_2$Br), ligand (Me$_6$TREN), in ratio of [Monomer:1:0.05:0.18] and solvent (isopropanol, 50 wt %) were charged to a Schlenk tube in the following order: deactivator, ligand, initiator, monomer, solvent. After sealing with a rubber septum and purging the mixture under inert atmosphere for at least 30 min, 5 cm of pre-activated Cu wire (0.25 mm) wrapped in a magnetic stirrer was added. The reaction mixture was then placed in an oil bath set to 25° C. and left to stir until full conversion. Conversion was measured by $^1$H NMR spectroscopy and SEC analysis was carried out with samples diluted in THF which were filtered over basic alumina prior to analysis to remove residual copper species Test Data Polymers having the general structure shown below were prepared as described above, varying reactant ratios to give the desired values of p and r, and varying monomer choice to give the desired value of q.

Details of the polymers are shown in the table below.

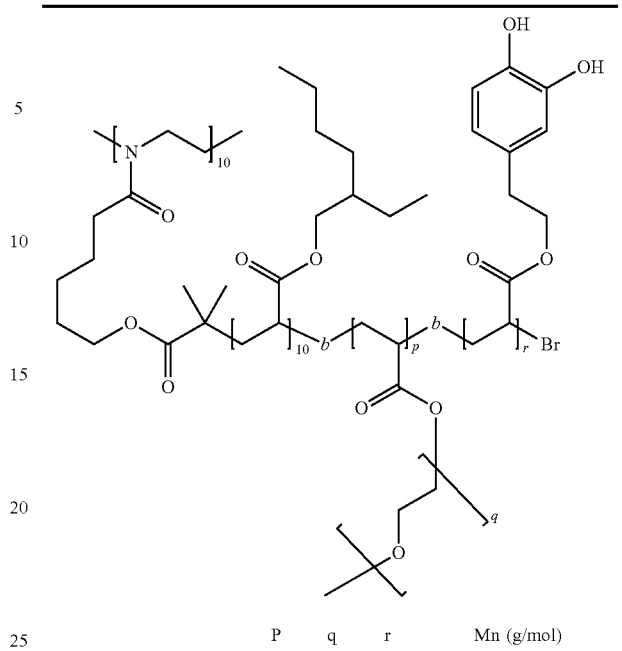

| | P | q | r | Mn (g/mol) |
|---|---|---|---|---|
| Polymer 4 | 0 | 0 | 0 | 14100 |
| Polymer 5 | 3 | 2 | 0 | 15100 |
| Polymer 6 | 7 | 2 | 0 | 23000 |
| Polymer 7 | 9 | 2 | 0 | 27900 |
| Polymer 8 | 1 | 3 | 0 | 16900 |
| Polymer 9 | 3 | 3 | 0 | 21000 |
| Polymer 10 | 5 | 3 | 0 | 25000 |
| Polymer 11 | 5 | 7 | 0 | 10000 |
| Polymer 12 | 0 | 0 | 1 | 12700 |
| Polymer 13 | 0 | 0 | 1 | 17000 |

1 g of each polymer was added to 99 g of an API Group I mineral oil. These samples were subjected to traction testing together with a sample of the same mineral oil without the addition of any polymer.

Each oil was tested using a Mini Traction Machine (MTM) available from PCS Instruments, London, UK. This machine employs a ⅜ inch diameter ball as an upper specimen which is run under an applied load against a lower specimen in the form of a disc. Both ball and disc are driven independently, allowing a range of slide to roll ratios to be achieved. The ball and disc are made of AISI 52100 polished steel. The test conditions are given in the table below:

| Load | | | 30N |
|---|---|---|---|
| Contact pressure | | | 0.9 GPa |
| Test duration | | | 45 minutes |
| Step | Type | Temperature (° C.) | Rolling speed (mm/s) |
| 1 | Traction | 40 | 1000 |
| 2 | Traction | 60 | 1000 |
| 3 | Stribeck | 60 | 20-2000 |
| 4 | Traction | 80 | 1000 |
| 5 | Stribeck | 80 | 20-2000 |
| 6 | Traction | 100 | 1000 |
| 7 | Stribeck | 100 | 20-2000 |
| 8 | Traction | 135 | 1000 |
| 9 | Stribeck | 135 | 20-2000 |

The MTM machine is equipped with a piezoelectric transducer which gives a measurement of the co-efficient of friction between the ball and the disc. Friction results are shown in the table below where each value is the average of at least two tests using each test oil. The data reported is the 20 min/s data point from the 100° C. Stribeck step (Step 7).

| Test Oil | Friction co-efficient at 20 mm/s and 100° C. |
|---|---|
| Base oil (no polymer) | 0.0965 |
| Polymer 4 | 0.0819 |
| Polymer 5 | 0.0584 |
| Polymer 6 | 0.0493 |
| Polymer 7 | 0.0612 |
| Polymer 8 | 0.0731 |
| Polymer 9 | 0.0663 |
| Polymer 10 | 0.0508 |
| Polymer 11 | 0.0447 |
| Polymer 12 | 0.0761 |
| Polymer 13 | 0.0756 |

It is clear that the polymers of the invention led to a significant reduction in the friction coefficient measured on the test samples compared to the base oil alone, indicating a greater separation of the contacting surfaces.

What is claimed is:

1. A polymer comprising 2 to 200 units having the structure (I):

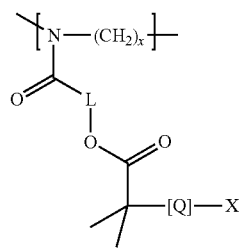
(I)

wherein x is 2 or 3, wherein L is $(CH_2)_y$, where y is an integer from 1 to 10, or wherein L is $CH(CH_3)CH_2S(CH_2)_z$, where z is an integer from 1 to 5;

wherein [Q] is absent or is a polymerised moiety consisting of units having the structure (II):

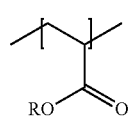
(II)

wherein R is a hydrocarbyl group, or a hydrocarbyl group containing one or more heteroatoms, wherein R may be linear, branched or cyclic, saturated or unsaturated, and wherein R has from 1 to 30 carbon atoms;

wherein [Q] either consists of identical units of structure (II), or wherein [Q] consists of more than one different unit of structure (II), differing in group R;

and wherein X is a halogen or another chain terminating group.

2. The polymer according to claim 1, wherein the number of units (II) in [Q] is from 2 to 200.

3. The polymer according to claim 1, further comprising units having the structure (III):

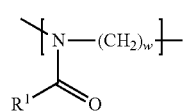
(III)

wherein $R^1$ is a linear or branched, saturated or unsaturated hydrocarbyl group having from 2 to 24 carbon atoms; and wherein w is 2 or 3.

4. The polymer according to claim 3 wherein the ratio of the number of units of structure (I) to the number of units of structure (III) in the polymer is from 1:100 to 100:1.

5. The polymer according to claim 1, consisting of units of structure (I).

6. The polymer according to claim 3, consisting of units of structure (I) and units of structure (III).

7. The polymer according to claim 1, wherein X is a bromine atom.

8. The polymer according to claim 1, having a number average molecular weight of 500 to 500,000 g/mol, as measured by Gel Permeation Chromatography with reference to linear narrow poly(methylmethacrylate) standards in the range of 550 to 600,000 g/mol.

9. A lubricating composition comprising a major amount of more than 50 percent by mass, based on the mass of the composition, of a base lubricant and a minor amount of less than 50 percent by mass, based on the mass of the composition, of the polymer according to claim 1.

10. The lubricating composition according to claim 9 which is a lubricating oil composition wherein the base lubricant is an oil of lubricating viscosity.

11. A method of reducing the friction and/or wear between contacting surfaces of a mechanical device, the method comprising lubricating the surfaces with the lubricating composition according to claim 9.

12. A compound of structure (IV):

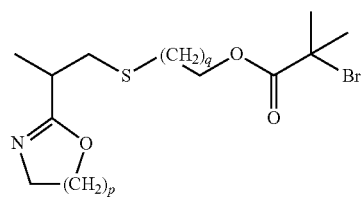
(IV)

where p is 1 or 2, and where q is an integer from 1 to 10.

13. A compound of structure (V):

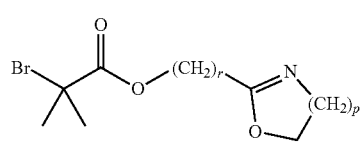
(V)

where p is 1 or 2, and where r is an integer from 4 to 10.

14. A method for synthesising a compound of structure (IV);

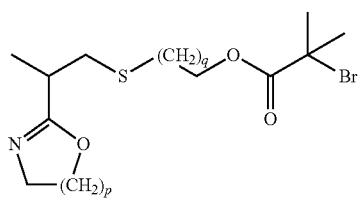

where p is 1 or 2, and where q is an integer from 1 to 10; the method comprising:
(a) reacting 2-isopropenyl-2-oxazoline, 2-isopropenyl-5,6-dihydro-4H-1,3-oxazine or a mixture thereof, with a mercapto alcohol;
(b) performing a Steglich esterification reaction by reacting the product of step (a) with α-bromoisobutyric acid, in the presence of 4-N,N-dimethylaminopyridine and a dihydrocarbyldiimide.

15. A method for synthesising a compound of structure (V);

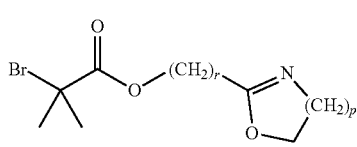

where p is 1 or 2, and where r is an integer from 4 to 10; the method comprising:
(a) ring-opening a lactone via reaction with 2-amino-1-ethanol, 3-amino-1-propanol, or a mixture thereof;
(b) ring-closing the product of step (a) via an organometallic-catalysed condensation-cyclisation reaction by heating in the presence of transition metal catalyst, preferably Ti(OnBu)$_4$;
(c) performing a Steglich esterification reaction by reacting the product of step (b) with a α-bromoisobutyric acid, in the presence of 4-N,N-dimethylaminopyridine and a dihydrocarbyldiimide.

16. The polymer according to claim 1, having a number average molecular weight of 5000 to 500,000 g/mol, as measured by Gel Permeation Chromatography with reference to linear narrow poly(methylmethacrylate) standards in the range of 550 to 600,000 g/mol.

17. The polymer according to claim 1, having a number average molecular weight of 10,000 to 500,000 g/mol, as measured by Gel Permeation Chromatography with reference to linear narrow poly(methylmethacrylate) standards in the range of 550 to 600,000 g/mol.

18. The polymer according to claim 1, wherein the number of units (I) is from 2 to 100.

19. The polymer according to claim 1, said polymer having 10 units of structure (I) and where [Q] consists of 20 units of structure (II) where each group R is 2-ethylhexyl.

20. The polymer according to claim 1, said polymer having 50 units of structure (I) and where [Q] consists of 5 units of structure (II) where each group R is 2-ethylhexyl.

21. The polymer according to claim 1, said polymer having 10 units of structure (I) and where [Q] consists of 10 units of structure (II) where each group R is 2-ethylhexyl.

22. The polymer according to claim 1, said polymer having 10 units of structure (I) and where [Q] consists of 10 units of structure (II) where each group R is 2-ethylhexyl and a single terminal unit of structure (II) where R is a catechol group.

23. The polymer according to claim 1, said polymer having 10 units of structure (I) and where [Q] consists of a random copolymer of 10 units of structure (II) where each group R is 2-ethylhexyl and 5 units of structure (II) where each group R is heptadecylethyleneglycol methyl ether.

24. The polymer according to claim 1, wherein the number of units (I) is from 5 to 200.

25. The polymer according to claim 1, wherein the number of units (I) is from 5 to 30.

26. The polymer according to claim 1, wherein L is (CH$_2$)$_y$ and y is an integer from 2 to 7.

27. The polymer having an Mn of 10,700 to 33,700 g/mol represented by the formula:

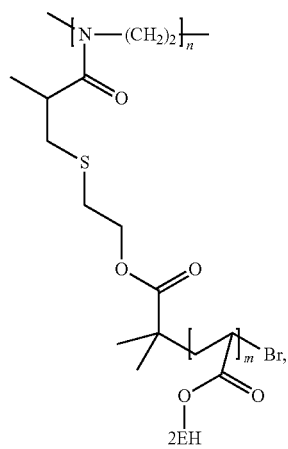

where m is 5 to 15, n is 10 to 50 and 2EH is 2-ethylhexyl, and the ratio of n:m is from 1.33 to 10.

28. The polymer having an Mn of 14,100 to 27,900 g/mol represented by the formula:

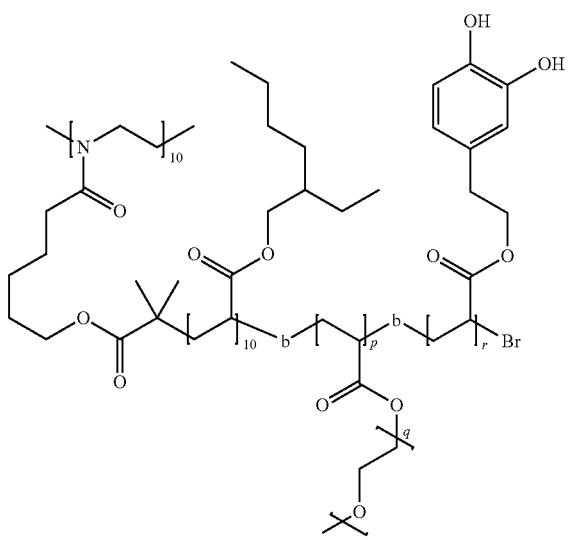

where p is 0 to 9, q is 0 to 7 and r is 0 or 1.

29. The lubricating composition according to claim 9 which is a lubricating oil composition wherein the base lubricant is Group I, II or III base stock.

30. The polymer according to claim 1, wherein L is $CH(CH_3)CH_2S(CH_2)_z$ where z is 1 to 5.

* * * * *